United States Patent
Lemann et al.

(12)

(10) Patent No.: US 6,326,013 B1
(45) Date of Patent: Dec. 4, 2001

(54) COSMETIC COMPOSITION IN THE FORM OF AN EMULSION COMPRISING A DISPERSION OF SURFACE-STABILIZED POLYMER PARTICLES IN A LIQUID FATTY PHASE

(75) Inventors: Patricia Lemann, Creteil; Valerie De La Polerie, Le Chatelet en Brie, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/399,734

(22) Filed: Sep. 20, 1999

(30) Foreign Application Priority Data

Sep. 18, 1998 (FR) .................................................. 98 11694

(51) Int. Cl.[7] ............................... A61K 7/00; A61K 7/02; A61K 7/021; A61K 7/027; A61K 7/031
(52) U.S. Cl. .................... 424/401; 424/78.02; 424/70.7; 424/70.11; 424/70.12; 424/70.22; 424/78.03; 424/70.16
(58) Field of Search ........................... 424/401, 70, 70.7, 424/78.02, 70.16, 70.11, 70.12, 70.22, 78.03

(56) References Cited

U.S. PATENT DOCUMENTS 5,945,095 * 1/1997 Mougin et al. ...................... 424/78.2
5,955,003 * 1/1998 Terren et al. ...................... 424/70.11
6,133,463 * 12/1993 Fourneron et al. .................. 424/401

FOREIGN PATENT DOCUMENTS 0 749 746 * 12/1996 (EP) .
0 749 747 * 12/1996 (EP) .
WO 94/12190 * 6/1994 (WO) .
WO 98/38981 * 9/1998 (WO) .

* cited by examiner

Primary Examiner—Diana Dudash
Assistant Examiner—Mina Haghighatian
(74) Attorney, Agent, or Firm—Oblon, Spivak, McClelland, Maier & Neustadt, P.C.

(57) ABSTRACT

A composition for topical application, comprising a liquid fatty phase and an aqueous phase, one of the phases being dispersed in the other phase, and said liquid fatty phase comprising surface-stabilized polymer particles in an amount sufficient to confer transfer-free properties to the composition.

26 Claims, No Drawings

COSMETIC COMPOSITION IN THE FORM OF AN EMULSION COMPRISING A DISPERSION OF SURFACE-STABILIZED POLYMER PARTICLES IN A LIQUID FATTY PHASE

BACKGROUND OF THE INVENTION

Field of the Invention

The present invention relates to a composition in the form of an emulsion comprising a polymer which is dispersed in a fatty phase, which composition is useful, in particular, in the cosmetic, dermatological, pharmaceutical and hygiene fields. More especially, the invention relates to a transfer-free composition for the care and/or make-up of the skin, both of the human face and of the human body, for mucous membranes such as the lips and the interior of the lower eyelids, and for keratinous fibers such as the eyelashes, eyebrows and hair.

The present composition can be provided, in particular, in the form of a more or less fluid cream or paste such as a liquid lipstick or a foundation, an eyeliner, a mascara, a sun protection composition, a composition for the artificial tanning of the skin or as a composition for making-up the body, and also as an eyeshadows or a facial powder. The present composition exhibits transfer-free properties in combination with a freshness effect and provides improved comfort with respect to known products.

Detailed Description of the Preferred Embodiments

Products for the make-up or care of the skin or lips of human beings such as foundations or lipsticks, generally comprise fatty phases such as waxes and oils, pigments and/or fillers and, optionally, additives such as cosmetic or dermatological active principles. They can also comprise so-called "pasty" products which have a supple consistency which makes it possible to produce colored or non-colored pastes which are to be applied with a brush.

These known compositions, when they are applied to the skin or the lips, exhibit the disadvantage of transferring, that is to say of being at least partly deposited and leaving traces on certain substrates with which they can be brought into contact, in particular a glass, a cup, a cigarette, an item of clothing or the skin. This transfer process results in mediocre persistence of the applied film, and results in the need for regular renewal, by application, of the foundation or lipstick composition to the skin or lips. Furthermore, the appearance of these unacceptable traces, in particular on blouse collars, can dissuade some women from using this type of make-up.

For some years, cosmetic scientists have been interested in lipstick compositions and more recently in foundation compositions which are "transfer-free". Thus, Shiseido describes, in Japanese Patent Application JP 61-65809, "transfer-free" lipstick compositions which comprise a siloxysilicate resin (with a three-dimensional network), a volatile silicone oil with a cyclic silicone chain and pulverulent fillers. Likewise, Noevier discloses in JP 62-61911, a "transfer-free" lipstick, eyeliner and foundation composition comprising one or more volatile silicones in combination with one or more hydrocarbon-comprising waxes.

These compositions, although exhibiting improved "transfer-free" properties, have the disadvantage of leaving on the lips, after evaporation of the silicone oils, a film which becomes uncomfortable over time (feeling of drying out and of tautness), which dissuades a number of women from choosing this type of lipstick. In order to improve the comfort of this type of composition on the skin or lips, non-volatile silicone or non-silicone oils can be added thereto, but, in this specific case, "transfer-free" efficiency is lost.

More recently, Procter & Gamble in Patent Application WO 96/36323 discloses mascara compositions of the water-in-oil emulsion type which exhibit a lengthy hold and resistance to water and which do not leave traces. These compositions comprise, inter alia, an aqueous polymer dispersion, generally known as a latex, in combination with a surfactant of the alkyl or alkoxy dimethicone copolyol type, hydrocarbon-comprising oils, pigments and fillers, as well as waxes. The transfer-free properties of the films deposited are not perfect. In particular, pronounced pressure or rubbing results in a decrease in the color of the deposit and in a redeposition on the substrate brought into contact with these films.

In addition, so-called "transfer-free" anhydrous compositions comprising a styrene-ethylene-propylene block polymer in combination with waxes, light or volatile oils, and pigments are known as disclosed in EP 0 497 144 and FR 2,357,244. These compositions exhibit the disadvantages of being not very comfortable, of having indifferent cosmetic properties, of being greasy and of being difficult to formulate. Furthermore, the "transfer-free" properties of these compositions are very mediocre.

More recently, EP 0 775 483 discloses compositions for the lips in the form of an aqueous dispersion of film-forming polymer. These compositions exhibit significant "transfer-free" properties and result in glossy films which are much appreciated by users. Unfortunately, these films exhibit disadvantage of being uncomfortable over time, after evaporation of the water.

A need, therefore, continues to exist for a composition which does not exhibit the above disadvantages and which has in particular notable "transfer-free" properties, even during pronounced pressure or rubbing, and a more or less glossy appearance, suited to the wish of the user, which does not dry out the skin or the lips on which it is applied, either during application or over time.

SUMMARY OF THE INVENTION

Accordingly, one object of the present invention is to provide a composition for topical application, which even during pronounced pressure or rubbing exhibits transfer-free properties and a more or less glossy appearance, which does not dry out the skin or the lips on which it is applied, either during application or over time.

Briefly, this object and other objects of the present invention as hereinafter will become more readily apparent can be attained by a composition for topical application comprising a liquid fatty phase and an aqueous phase, one of the phases being dispersed in the other phase, and said liquid fatty phase comprising surface-stabilized polymer particles in an amount sufficient to confer transfer-free properties to the composition.

DETAILED DESCRIPTION OF THE PREFERRED EMBODIMENTS

It has now been found that the use of an emulsion comprising a dispersible polymer in the liquid fatty phase makes it possible to obtain a cosmetic, dermatological, pharmaceutical or hygiene composition which results in a cohesive coating having very good adhesion characteristics, which does not transfer at all and which is resistant to water, while being very pleasant on application and upon wear throughout the day. The topical coating is in particular neither greasy nor dry, and is flexible and non-sticky. In addition, the composition of the invention exhibits properties of comfort on application and over time and in particular properties of freshness on application, of moisturization and of absence of feelings of tautness.

The amount of polymer in the composition must be sufficient to form, on the skin and/or lips and/or keratinous fibers, a film capable of trapping coloring materials and/or cosmetic or dermatological active ingredients and/or oils for the purpose of limiting, indeed even eliminating, their transfer onto a substrate with which the film is brought into contact. The amount of polymer depends on the amount of coloring materials and/or of active ingredients and/or of oils present in the composition. In practice, the amount of polymer is present in an amount greater than 2% by weight, as the active material, with respect to the total weight of the composition.

The composition of the invention is a homogeneous dispersion of a liquid fatty phase in a continuous aqueous phase or a homogeneous dispersion of an aqueous phase in a continuous liquid fatty phase. The dispersion is prepared by any means and in particular by use of an emulsifier, particles or vesicles. More especially, the composition is an oil-in-water (O/W) or water-in-oil (W/O) emulsion. It can also be a multiple emulsion and in particular a triple emulsion.

This composition is in particular useful as a cosmetic, dermatological, hygienic or pharmaceutical composition. It, therefore, comprises ingredients which are compatible with the skin, mucous membranes and keratinous fibers.

Another aspect of the invention is the use, in a cosmetic composition or in the manufacture of a dermatological composition in the form of a dispersion of a first phase in a second phase, one of the first and second phases being a liquid fatty phase, of a sufficient amount of surface-stabilized polymer particles in the said liquid fatty phase, in order to decrease, indeed even eliminate, the transfer of a composition film spread onto a mucous membrane such as the lips, and/or on the skin of human beings and/or keratinous fibers to a substrate brought into contact with the film.

The composition advantageously comprises at least one ingredient selected from cosmetic, dermatological, hygienic and pharmaceutically active substances, coloring materials and their mixtures. By virtue of the dispersion of surface-stabilized polymer particles present in the liquid fatty phase, the composition of the invention makes it possible to limit, indeed even eliminate, the transfer of applied composition and in particular the transfer of the active ingredients and/or of the coloring materials. Accordingly, the active ingredients and/or coloring materials of the applied composition remain on the surface where they were deposited.

Another aspect of the invention is a process for the cosmetic care of or for the making-up of the lips and/or skin and/or keratinous fibers which consists in applying, to the lips and/or skin and/or fibers respectively, a cosmetic composition as defined above.

A further aspect of the invention is a cosmetic process for limiting, indeed even eliminating, the transfer of a composition for making-up or for caring for the skin and/or lips and/or keratinous fibers onto a substrate other than the skin and/or lips and/or fibers, the composition comprising a liquid fatty phase and an aqueous phase, one of the phases being dispersed in the other phase, and said liquid fatty phase comprising surface-stabilized polymer particles in an amount sufficient to confer transfer-free properties to the composition.

The polymer used in the present application can be almost any type. It is thus possible to employ a polymer produced by radical polymerization, a polycondensate, indeed even a polymer of natural origin, and their mixtures. The polymer can be selected by one of skill in the art as a function of its properties and according to the subsequent application desired for the composition. The polymer selected preferably is one which is able to form a film. However, it is possible to use a polymer which is unable to form a film.

The term "polymer which is unable to form a film" is understood to mean a polymer which is not capable alone of forming an isolable film. This polymer makes it possible, in combination with a nonvolatile compound of the oil type, to form a continuous and homogeneous coating on the skin and mucous membranes.

The polymer is advantageously provided in the form of dispersed particles which are stabilized on a surface by at least one stabilizing agent.

One advantage of the use of a dispersion of particles in a composition of the invention is that the particles remain in the state of individual particles, without forming agglomerates, in the fatty phase, which would not be the case with inorganic particles of nanometric size. Another advantage of the polymer dispersion is the possibility of obtaining very fluid compositions (of the order of 130 centipoises), even in the presence of a high level of polymer.

Yet another advantage of such a dispersion is that it is possible to grade, as desired, the size of the polymer particles and to adjust their "polydispersity" in size during synthesis. It is thus possible to obtain particles of very small size, which are invisible to the naked eye when they are in the composition and when they are applied to the skin or lips. This would be impossible with pigments in particulate form, their composition not allowing the mean size of the particles to be varied.

In addition, it has been found that the composition of the invention exhibits particularly advantageous qualities of spreading over and of adhesion to the skin or mucous membranes, as well as providing spreadings which are smooth and pleasant to touch. These compositions have, in addition, the advantage of being easy to remove, in particular, with a conventional make-up removal milk. This is indeed remarkable, since the compositions of the prior art with high "transfer-free" properties are very difficult to remove. In general, they are sold with a specific make-up removal product, which introduces an additional restriction for the user.

The composition of the invention thus advantageously comprises a stable dispersion of generally spherical particles of at least one polymer in a physiologically acceptable liquid fatty phase These dispersions can in particular be provided in the form of nanoparticles of polymers as a stable dispersion in the fatty phase. The nanoparticles preferably have a size ranging from 5–600 nm, in view of the fact that, beyond approximately 600 nm, the dispersions of particles become much less stable.

A further advantage of the polymer dispersion of the composition of the invention is the possibility of varying the glass transition temperature (Tg) of the polymer or of the polymeric system (polymer plus additive of the plasticizer type) and of thus changing from a soft polymer to a more or less hard polymer, making it possible to adjust the mechanical properties of the composition as a function of the envisaged application.

The polymers which can be used in the composition of the invention preferably have a molecular weight of the order of 2,000–10,000,000 and a Tg of −100° C. to 300° C., preferably from −10° C. to 50° C.

It is possible to use polymers which are able to form films, preferably having a low Tg of less than or equal to the temperature of the skin, in particular of less than 40° C. A dispersion is thus obtained which is able to form a film when it is applied to a surface of a substrate, which is not the case when use is made of dispersions of inorganic pigments employed in the prior art.

When the polymer exhibits a glass transition temperature which is too high for the desired application it is possible to combine it with a plasticizer, so as to lower the temperature of the mixture used. The plasticizer can be selected from plasticizers normally used in the field of application and in particular from compounds which can be solvents of the polymer.

Suitable such polymers which are able to form films, of acrylic or vinyl radical homopolymers or copolymers, preferably have a Tg $\geq$ 40° C. and in particular ranging from −10° C. to 30° C.

Suitable polymers which are unable to form films include optionally crosslinked, vinyl or acrylic, radical homopolymers or copolymers preferably having a Tg $\geq$ 40° C. and in particular ranging from 45–150° C.

The term "radical polymer" is understood to mean a polymer which is prepared by polymerization of monomers which in particular have ethylenic unsaturation, each monomer being capable of undergoing homopolymerization (unlike polycondensates). Suitable radical polymers include vinyl polymers or copolymers, and in particular acrylic polymers. The vinyl polymers may be prepared by the polymerization of monomers having ethylenic unsaturation and at least one acid group and/or esters of these acid monomers and/or amides of these acids.

Suitable such acid group containing monomers include α,β-ethylenic unsaturated carboxylic acids such as acrylic acid, methacrylic acid, crotonic acid, maleic acid and itaconic acid. Preferred monomers include (meth)acrylic acid and crotonic acid and more preferably (meth)acrylic acid.

Suitable esters of acid monomers advantageously include the $C_1$–$C_{20}$-alkyl, preferably the $C_1$–$C_8$-alkyl (meth)acrylates, the aryl, particularly the $C_6$–$C_{10}$ aryl (meth)acrylates and the hydroxyalkyl, particularly the $C_2$–$C_6$ hydroxyalkyl (meth)acrylates. Particularly suitable alkyl (meth)acrylates include the methyl, ethyl, butyl, isobutyl, 2-ethylhexyl and lauryl (meth)acrylate esters. Particularly suitable hydroxyalkyl (meth)acrylates include the hydroxyethyl (meth)acrylate and 2-hydroxypropyl (meth)acrylate ersters. Particularly suitable aryl (meth)acrylates include the benzyl and phenyl acrylate esters.

The particularly preferred esters of (meth)acrylic acid are the alkyl (meth)acrylates.

A preferred radical polymer is a copolymer of (meth)acrylic acid and an alkyl, particularly a $C_1$–$C_4$ alkyl, (meth)acrylate. Most preferred is methyl acrylate, optionally copolymerized with acrylic acid.

Suitable amides of the acid monomers include the (meth)acrylamides such as the N-alkyl(meth)acrylamides, in particular N-($C_2$–$C_{12}$ alkyl)(meth)acrylamides such as N-ethylacrylamide, N-(t-butyl)acrylamide and N-octylacrylamide, and N,N-di($C_1$–$C_4$ alkyl)(meth)acrylamides.

Suitable vinyl polymers also include those formed by the polymerization of ethylenically unsaturated monomers having at least one amine group, in the free form or else partially or completely neutralized, or alternatively partially or completely quaternized. Such monomers include, for example, dimethylaminoethyl (meth)acrylate, (dimethylaminoethyl) methacrylamide, vinylamine, vinylpyridine diallyldimethylammonium chloride.

Suitable vinyl polymers also include those prepared by the homopolymerization or by the copolymerization of at least one monomer selected from vinyl esters and styrene monomers. In particular, these monomers can be polymerized with acid monomers and/or their esters and/or their amides, such as those mentioned above. Suitable vinyl esters include vinyl acetate, vinyl propionate, vinyl neodecanoate, vinyl pivalate, vinyl benzoate and vinyl t-butylbenzoate; and suitable styrene monomers include styrene and alpha-methylstyrene.

The list of the monomers presented above is not limiting and it is possible to use any monomer known to one of skill in the art which is within the categories of acrylic and vinyl monomers (including monomers modified with a silicone chain).

Suitable such other vinyl monomers include:

N-vinylpyrrolidone, vinylcaprolactam, N-($C_1$–$C_6$ alkyl) vinylpyrroles, vinyloxazoles, vinylthiazoles, vinylpyrimidines and vinylimidazoles, and olefins such as ethylene, propylene, butylene, isoprene and butadiene.

The vinyl polymer may be crosslinked by a difunctional monomer containing, in particular, at least two sites of ethylenic unsaturation such as ethylene glycol dimethacrylate and diallyl phthalate.

The polymers of the invention may also be selected, without implied limitation, from the following polymers or copolymers: polyurethanes, polyurethane-acrylics, polyureas, polyurea-polyurethanes, polyester polyurethanes, polyether-polyurethanes, polyesters, polyesteramides, polyesters with a fatty chain or alkyds; acrylic and/or vinyl polymers or copolymers; acrylic-silicone copolymers; polyacrylamides; silicone polymers, fluorinated polymers and their mixtures.

The liquid fatty phase in which the polymer is dispersed can be composed of any cosmetically or dermatologically acceptable oil, and more generally a physiologically acceptable oil, selected in particular from carbon-comprising, hydrocarbon-comprising, fluorinated and/or silicone oils of mineral, animal, plant or synthetic origin, alone or as a mixture insofar as they form a homogeneous and stable mixture and insofar as they are compatible for the purpose envisaged.

The term "liquid fatty phase" is understood to mean any non-aqueous medium which is liquid at room temperature (25° C.) and atmospheric pressure. Suitable such liquid fatty phases are comprised of hydrocarbon oils such as a liquid paraffin or a liquid petrolatum, mink oil, turtle oil, soybean oil, perhydrosqualene, sweet almond oil, calophyllum oil, palm oil, grape seed oil, sesame oil, maize oil, parlean oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters such as isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, di(2-ethylhexyl) succinate, diusostearyl malate, glyceryl triisostearate or diglyceryl triisostearate;

higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol, linoleyl or linolenyl alcohol, isostearyl alcohol or octyldodecanol; silicone oils such as polydimethylsiloxanes (PDMS), which siloxanes are optionally phenylated such as phenyltrimethicones, or are optionally substituted by optionally fluorinated aliphatic and/or aromatic groups or by functional groups such as hydroxyl, thiol and/or amine groups; polysiloxanes modified by fatty acids, fatty alcohols or polyoxyalkylenes, fluorinated silicones or perfluorinated oils.

The oil phase may comprise one or more oils which are volatile at room temperature. The term "volatile oil phase" is understood to mean any nonaqueous medium which is capable of evaporating from the skin or lips or fibers at room temperature. This volatile phase comprises, in particular, oils having a vapor pressure at room temperature and atmospheric pressure ranging from $10^{-3}$ to 300 mm of Hg (0.13 Pa to 40,000 Pa). These volatile oils facilitate, in particular, the application of the composition to the skin, mucous membranes or keratinous fibers. These oils can be hydrocarbon-comprising oils, silicone oils optionally comprising alkyl or alkoxy groups in a pendant position or at the end of the silicone chain, or fluorinated oils.

Suitable volatile silicone oils which can be used in the invention include linear or cyclic silicones having from 2–7 silicon atoms, these silicones optionally comprising alkyl or alkoxy groups having from 1–10 carbon atoms, and $C_8$–$C_{16}$ isoparaffins. These volatile oils represent, in particular, from 5–97.5% of the total weight of the composition, more preferably from 20–75%. Suitable volatile oils of the invention include, in particular, octamethylcyclotetrasiloxane, decamethylcyclopentasiloxane, hexadecamethylcyclohexasiloxane, heptamethylhexyltrisiloxane, heptamethyloctyltrisiloxane or $C_8$–$C_{16}$ isoparaffins such as "Isopars", Permetyls and in particular isododecane.

In a specific embodiment of the invention, the liquid fatty phase is selected from the group consisting of:
- non-aqueous liquid compounds having an overall solubility parameter according to the Hansen solubility space of less than 17 $(MPa)^{1/2}$, or
- monoalcohols having an overall Volubility parameter according to the Hansen Volubility space of less than or equal to 20 $(MPa)^{1/2}$, or their mixtures.

The overall Volubility parameter δ according to the Hansen Volubility space is defined in the article "Solubility parameter values" by Eric A. Grulke in the work "Polymer Handbook", 3rd edition, Chapter VII, pages 519–559, by the relationship:

$$\delta = (d_D^2 + d_p^2 + d_H^2)^{1/2}$$

in which:
- $d_D$ characterizes the London dispersion forces resulting from the formation of dipoles induced during molecular impacts,
- $d_p$ characterizes the forces of Debye interactions between permanent dipoles,
- do characterizes the forces of specific interactions such as hydrogen bond, acid/base or donor/acceptor type interactions and the like. The definition of the solvents in the three dimensional solubility space according to Hansen is described in the article by C. M. Hansen: "The three dimensional solubility parameters", J. Paint Technol., 39, 105 (1967).

Suitable liquid fatty phases having an overall solubility parameter according to the Hansen solubility space of less than or equal to 17 $(MPa)^{1/2}$ include vegetable oils formed by esters of fatty acids and polyols, in particular triglycerides such as sunflower oil, sesame oil and rapeseed oil, or esters derived from long-chain acids and alcohols, which alcohols contain from 6–20 carbon atoms, in particular esters of the formula: $RCOOR^1$, wherein R represents the residue of a higher fatty acid having from 7–19 carbon atoms and $R^1$ represents a hydrocarbon-comprising chain comprising from 3–20 carbon atoms such as palmitates, adipates and benzoates, in particular diisopropyl adipate. Also included are hydrocarbons and in particular of liquid paraffin, liquid petrolatum or hydrogenated polyisobutylene, isododecane, or alternatively "Isopars", and volatile isoparaffins. Further included are silicone oils such as polydimethylsiloxanes and polymethylphenylsiloxanes, optionally substituted by optionally fluorinated aliphatic and/or aromatic groups or by functional groups such as hydroxyl, thiol and/or amine groups, and volatile silicone oils, in particular, cyclic oils. Still further included are solvents, alone or in admixture, selected from (i) linear, branched or cyclic esters having more than 6 carbon atoms, (ii) ethers having more than 6 carbon atoms, and (iii) ketones having more than 6 carbon atoms. The term "monoalcohols having an overall solubility parameter according to the Hansen solubility space of less than or equal to 20 $(MPa)^{1/2}$" is understood to mean aliphatic fatty alcohols having at least 6 carbon atoms, the hydrocarbon-comprising chain not having a substituent. Suitable monoalcohols include oleyl alcohol, decanol, dodecanol, octadecanol and linoleyl alcohol.

With respect to non-aqueous media, those disclosed in FR 2,710,646 of L.V.M.H. may be used.

The choice of a non-aqueous medium is made by one of skill in the art according to the nature of the monomers which constitute the polymer and/or the nature of the stabilizing agent, as indicated as follows.

Furthermore, the total liquid fatty phase in which the polymer is dispersed can represent from 5–97.5% of the total weight of the composition, preferably from 20–75%. The non-volatile part represents at least 0% and in practice from 1–50% of the total weight of the composition. This fatty phase comprises one or more oils which are compatible with each another.

The polymer dispersion can be manufactured as disclosed in EP 0 749 747. Polymerization can be conducted as a dispersion, that is to say, by precipitation of the polymer during formation, with protection of the particles formed with a stabilizing agent.

A mixture comprising the starting monomers and a radical initiator is prepared. This mixture is dissolved in a solvent (identified hereinafter as "synthesis solvent"). When the fatty phase is a non-volatile oil, the polymerization can be conducted in a non-polar organic solvent (synthesis solvent), the non-volatile oil, which must be miscible with the synthesis solvent, can then be added and the synthesis solvent can be selectively distilled.

A synthesis solvent is thus selected so that the starting monomers and the radical initiator are soluble in the solvent and the polymer particles obtained are insoluble therein, in order for them to precipitate as they are formed. In particular, the solvent can be selected from alkanes such as isododecane and cyclohexane.

When the fatty phase selected comprises an oil, the polymerization can be conducted in the oil, which also acts as solvent. The monomers must also be soluble, as well as the radical initiator, and the polymer obtained must be insoluble therein.

The monomers are preferably present in the synthesis solvent, before polymerization, in an amount of 5–20% by weight of the reaction mixture. All the monomers can be present in the solvent before the beginning of the reaction or a portion of the monomers can be added as the polymerization reaction proceeds.

Suitable radical initiators for the reaction include, in particular, azobisisobutyronitrile and tert-butyl peroxy(2-ethylhexanoate).

The polymer particles are stabilized at the surface, during the polymerization, by virtue of a stabilizing agent which can be a sequential polymer, a grafted polymer and/or a random polymer, alone or in admixture. The stabilization can be conducted by any known means and in particular by direct addition of the sequential polymer, grafted polymer and/or random polymer during the polymerization.

The stabilizing agent is preferably also present in the mixture before polymerization. However it is also possible to add it continuously, in particular when the monomers are also added continuously.

The amount of stabilizing agent ranges from 2–30% by weight with respect to the starting mixture of monomers and preferably 5–20% by weight.

When a grafted and/or sequential polymer is used as the stabilizing agent, the synthesis solvent is selected such that at least a portion of the graft or sequence of the stabilizing polymer is soluble in the solvent, the other portion of the graft or sequence not ite being soluble therein. The stabilizing polymer employed during the polymerization must be soluble, or dispersible, in the synthesis solvent. Furthermore, the choice is preferably made of a stabilizing agent for which the insoluble sequence or graft exhibits a degree of affinity for the polymer formed during the polymerization.

Suitable grafted polymers include silicone polymers having a hydrocarbon comprising chain grafted thereto; or hydrocarbon-comprising polymers having a silicone chain grafted thereto.

Grafted copolymers having, for example, an insoluble backbone of the polyacrylic type with soluble grafts of poly(12-hydroxystearic acid) are also suitable.

A particularly useful grafted or sequential block copolymer is one which comprises at least one polyorganosiloxane block and at least one radical polymer block such as grafted copolymers of the acrylic/silicone type, which can be employed in particular when the non-aqueous medium is a silicone medium.

Also useful are grafted or sequential block copolymers comprising at least one polyorganosiloxane block and at least one polyether block. The polyorganopolysiloxane block can be, in particular, a polydimethylsiloxane or alternatively a poly($C_2$–$C_{18}$)alkylmethylsiloxane; and the polyether block can be a poly($C_2$–$C_{18}$ alkylene), in particular polyoxyethylene and/or polyoxypropylene. Particularly useful are dimethicone copolyols and ($C_2$–$C_{18}$)alkyl dimethicone copolyols such as those sold under the name "Dow Corning 3225C" by Dow Corning, and lauryl methicones such as those sold under the name "Dow Corning Q2-5200" by Dow Corning.

Other useful grafted or sequential block copolymers include those comprising at least one block resulting from the polymerization of at least one ethylenic monomer with one or more optionally conjugated ethylenic bonds such as ethylene or dienes, for example, butadiene or isoprene, and at least one block of a vinyl polymer and preferably a styrene polymer. When the ethylenic monomer comprises several optionally conjugated ethylenic bonds, the residual ethylenic sites of unsaturation, after the polymerization, are generally hydrogenated. Thus, in a known way, the polymerization of isoprene results, after hydrogenation, in the formation of an ethylene-propylene block and the polymerization of butadiene results, after hydrogenation, in the formation of an ethylene-butylene block. Suitable such polymers, of the sequential copolymers, in particular, are of the "diblock" or "triblock" type, which include polystyrene/polyisoprene and polystyrene/polybutadiene, such as those sold under the name of "Luvitol HSB" by BASF, of the polystyrene/copoly (ethylenepropylene) type, such as those sold under the name of "Kraton" by Shell Chemical Co. or of the polystyrene/copoly(ethylene-butylene) type. These copolymers are generally known as copolymers of a hydrogenated or non-hydrogenated diene.

Also included as grafted or sequential block copolymers are those which comprise at least one block resulting from the polymerization of at least one ethylenic monomer with one or more optionally conjugated ethylenic bonds such as ethylene or isobutylene, and at least one block of an acrylic polymer, of poly(methyl methacrylate)/polyisobutylene bi- or trisequential copolymers or of grafted copolymers with a poly(methyl methacrylate) backbone and with polyisobutylene grafts.

Such grafted or sequential block copolymers contain at least one block resulting from the polymerization of at least one ethylenic monomer with one or more optionally conjugated ethylenic bonds such as ethylene or dienes, and at least one block of a polyether such as a poly($C_2$–$C_{18}$ alkylene), in particular a polyoxyethylene and/or polyoxypropylene, of polyoxyethylene/polybutadiene or polyoxyethylene/polyisobutylene bi- or trisequential copolymers.

When a random polymer is used as stabilizing agent, it is selected so that it has a sufficient amount of groups which render it soluble in the envisaged synthesis solvent.

It is thus possible to employ copolymers based on alkyl acrylates or methacrylates resulting from $C_1$–$C_4$ alcohols and on alkyl acrylates or methacrylates resulting from $C_8$–$C_{30}$ alcohols. A preferred copolymer is stearyl methacrylate/ methyl methacrylate copolymer.

When the synthesis solvent is non-polar, the preferred selected stabilizing agent is a polymer which provides the most complete possible covering of the particles, several chains of stabilizing polymers then being adsorbed on one particle of polymer obtained by polymerization.

In this case, it is then preferable to use, as a stabilizing agent, either a grafted polymer or a sequential polymer, so as to provide a better interfacial activity. This is because the sequences or grafts which are insoluble in the synthesis solvent contribute a bulkier covering to the surface of the particles. Furthermore, when the liquid fatty phase comprises at least one silicone oil, the stabilizing agent is preferably selected from the group consisting of grafted or sequential block copolymers comprising at least one polyorganosiloxane block resulting from the polymerization of a siloxane and at least one block of a radical polymer or of a polyether or of a polyester such as polyoxypropylenated and/or polyoxyethylenated blocks.

When the liquid fatty phase does not comprise a silicone oil, the stabilizing agent is preferably selected from the group consisting of:
 (a) grafted or sequential block copolymers comprising at least one polyorganosiloxane block and at least one block of a radical polymer or of a polyether or of a polyester,
 (b) a copolymer of a $C_1$–$C_4$-alkyl acrylate or methacrylate or of a $C_8$–$C_{30}$-acrylate or methacrylate,
 (c) grafted or sequential block copolymers comprising at least one block resulting from the polymerization of at least one ethylenic monomer with at least one optionally conjugated ethylenic bond, and at least one block of a vinyl or acrylic polymer or of a polyether or of a polyester, or mixtures thereof.

Diblock polymers are preferably used.

The dispersions of the invention which have been prepared can then be used in a composition, in particular a cosmetic, dermatological, pharmaceutical and/or hygienic composition such as a composition for the care of or for the make-up of the skin or lips, or alternatively a hair composition or an anti-sun composition or a composition for the artificial tanning of the skin.

Depending on the application, it is possible to use dispersions of polymers, which are or are not able to form films, in volatile or non-volatile oils.

According to the invention, the liquid fatty phase described above can constitute the continuous phase of the composition or else the disperse phase. The other phase is an aqueous phase comprising water and optionally water-soluble solvents such as lower alcohols. In this case, these solvents cannot constitute the liquid fatty phase. This is because, in order to form the composition of the invention, the two phases have to be immiscible. The composition of the invention is advantageously of the W/O or O/W type.

These emulsions can be prepared by using a surfactant or a mixture of surfactants. The HLB (hydrophilic/lipophilic balance) is appropriate to the direction of the emulsion.

Suitable surfactant which can be used in the invention, appropriate for the production of a W/O emulsion, include those which have an HLB of less than 7 and in particular polyol fatty acid esters such as sorbitol or glycerol mono-, di-, tri- or sesquioleates or -stearates or glycerol or polyethylene glycol laurates; or alkyl or alkoxy dimethicone copolyols with an alkyl or alkoxy chain, in the pendant position or at the end of the silicone backbone, for example, having from 6–22 carbon atoms. Particularly suitable surfactants, which can be used in the invention for the production of an O/W emulsion, are those having an HLB of greater than 7 such as polyethylene glycol fatty acid esters (polyethylene glycol monostearate or monolaurate); polyoxyethylenated fatty acid esters (stearate, oleate) of sorbitol; polyoxyethylenated alkyl (lauryl, cetyl, stearyl, octyl) ethers and dimethicone copolyols. Generally any ionic (cationic or anionic) or amphoteric surfactant and any nonionic surfactant well known to those of skill in the art may be used.

The composition can advantageously comprise one or more coloring materials comprising one or more pulverulent compounds and/or one or more fat-soluble and/or water-soluble colorants, for example, in an amount of 0.01–70% of the total weight of the composition. The pulverulent compounds can be selected from pigments and/or pearlescent agents and/or fillers commonly used in cosmetic and dermatological compositions. The pulverulent compounds advantageously are present in an amount from 0.1–50% of the total weight of the composition, preferably from 1–30%. The smaller the amount of pulverulent compounds, the better the transfer-free and comfort qualities. The fact that the transfer-free properties are enhanced as the amount of pulverulent compounds decreases is entirely surprising. The reason for this is that, until now, the transfer-free properties of the compositions of the prior art had been enhanced with the amounts of pulverulent compounds included in the compositions. Conversely, the discomfort and dryness on the skin and mucous membranes because of the presence of the pulverulent compound containing compositions increased.

Furthermore, the transfer-free property is enhanced proportionately with the amount of polymer which is dispersible in the liquid fatty phase. In practice, the polymer can represent, as active material, up to 60% (as active material or dry matter) of the total weight of the composition. If more than 12% by weight of active polymer material and of non-volatile oil is present in the composition, a total transfer-free film is obtained. From 2–12%, the transfer-free effect is significant without, however, being total. The transfer-free properties can thus be adjusted as desired, which was impossible with the transfer-free compositions of the prior art, without detriment to the comfort of the film deposited.

The pigments can be white or colored, inorganic and/or organic, coated or uncoated. Suitable such inorganic pigments include titanium dioxide, optionally treated on its surface, or zirconium oxide or cerium oxide, as well as iron oxide or chromium oxide, manganese violet, ultramarine blue, chromium hydrate and ferric blue. Suitable organic pigments include carbon black, pigments of D & C type and lakes based on cochineal carmine or on barium, strontium, calcium or aluminum.

The pearlescent pigments can be selected from white pearlescent pigments such as mica covered with titanium oxide or with bismuth oxychloride, colored pearlescent pigments such as titanium oxide-coated mica coated with iron oxides, titanium oxide-coated mica coated with, in particular, ferric blue or chromium oxide, or titanium oxide-coated mica coated with an organic pigment of the above-mentioned type, as well as pearlescent pigments based on bismuth oxychloride.

The fillers can be inorganic or organic, lamellar or spherical. Suitable such fillers include talc, mica, silica, kaolin, nylon, poly-β-alanine and polyethylene powders, lauroyllysine, starch, boron nitride, tetrafluoroethylene polymer powders such as Teflon, hollow microspheres such as Expancel (Nobel Industrie), polybrap (Dow Corning) and silicone resin microbeads (Tospearls from Toshiba, for example), precipitated calcium carbonate, magnesium carbonate and carbonate hydroxide, hydroxyapatite, hollow silica microspheres (Silica Beads from Maprecos), glass or ceramic microcapsules, or metal soaps derived from organic carboxylic acids having from 8–22 carbon atoms, preferably from 12–18 carbon atoms, for example zinc, magnesium or lithium stearate, zinc laurate or magnesium myristate.

The fat-soluble colorants include, for example, Sudan red, DC Red 17, DC Green 6, β-carotene, soybean oil, Sudan brown, DC Yellow 11, DC Violet 2, DC Orange 5 or Quinoline yellow. They can represent from 0.01–20% of the weight of the composition, preferably from 0.1–6%. The water-soluble colorants include, for example, beetroot juice, methylene blue or carotene and can represent up to 6% of the total weight of the composition.

The polymer of the composition of the invention makes possible the formation of a film on the skin, lips and/or mucous membranes and/or fibers in a network which traps the coloring materials (including the fillers) and/or the active principles. Depending on the relative amount of coloring materials used taken with respect to the amount of stabilized polymer, it is possible to obtain a more or less glossy and more or less transfer-free film.

Suitable cosmetic, dermatological, hygienic or pharmaceutical active principles which can be used in the composition of the invention include moisturizing agents, vitamins, essential fatty acids, sphingolipids and sunscreen agents. These active principles are used in their normal amounts and in particular at concentrations of 0.001–20% of the total weight of the composition.

The composition of the invention can additionally comprise, according to the application envisaged, the constituents normally used in the fields under consideration, the type of conventionally which are present in an amount appropriate for the desired pharmaceutical dosage form.

In particular, it can comprise, in addition to the liquid fatty phase in which the polymer is stabilized, additional fatty phases selected from waxes, oils, gums and/or pasty fatty substances of plant, animal, mineral or synthetic origin, indeed silicone origin, and their mixtures.

Suitable waxes which are solid at room temperature and which can be present in the composition of the invention include hydrocarbon comprising waxes such as beeswax, carnauba wax, candelilla wax, ouricury wax, Japan wax, cork fibre or sugarcane waxes, paraffin or lignite waxes, microcrystalline waxes, lanolin wax, montan wax, ozokerites, polyethylene waxes, waxes obtained by the Fischer-Tropsch synthesis, hydrogenated oils, fatty esters and glycerides which are solid at 25° C. It is also possible to use silicone waxes which include alkyl, alkoxy and/or esters of polymethylsiloxane. The waxes can be provided in the form of stable dispersions of colloidal wax particles such that they can be prepared by known methods such as those described in "Microemulsions, Theory and Practice", edited by L. M. Prince, Academic Press (1977), pages 21–32. A particularly suitable wax which is liquid at room temperature is jojoba oil.

The waxes can be present in an amount of 0–50% by weight of the composition, preferably 10–30%.

The composition can additionally comprise any additive conventionally used in such compositions such as thickeners, antioxidants, fragrances, preservatives and fat-soluble polymers such as polyalkylenes, in particular, polybutene, polyacrylates and silicone polymers compatible with the fatty phase, as well as polyvinylpyrrolidone derivatives. Of course, one of skill in the art will carefully select one or more of such additives in the amounts desired so that the advantageous properties of the composition of the invention are not, or not substantially, detrimentally affected by the addition of such materials.

In a specific embodiment of the invention, the compositions of the invention can be prepared by method(s) known to those of skill in the art. They can be provided in the form of a simple or multiple emulsion with a continuous oily or aqueous phase or of an oily dispersion in an aqueous phase by virtue of vesicles comprising ionic and/or nonionic lipids. They can additionally have the appearance of a more or less fluid cream, of a more or less viscous paste or of a solid emulsion cast in a mold in the form of a dish or stick. The dynamic viscosity of the composition can be selected within a wide range from 0.001–800 Pa·s, measured at 25° C. with a viscometer equipped with a rotor rotating at 100 revolutions/min.

The composition of the invention can be a product for the make-up of the skin, lips or keratinous fibers such as foundations, face powders, eye shadows, mascaras, eyeliners, lipsticks and products for the make-up of the body (semi-permanent tattooing). These products can additionally comprise one or more cosmetic or dermatological active principles for the purpose of contributing a care valency to the make-up.

These compositions for topical application can furthermore constitute a cosmetic, dermatological, hygienic or pharmaceutical composition for protecting, treating or caring for the human face, neck, hands or body and can constitute, for example, a care cream, an antisun or artificial tanning product, a balm for caring for or protecting the lips, or a dermatological ointment or salve.

Having generally described this invention, a further understanding can be obtained by reference to certain specific examples which are provided herein for purposes of illustration only and are not intended to be limiting unless otherwise specified.

EXAMPLES

Example 1

(Polymer Dispersion)

A dispersion of non-crosslinked copolymer of methyl acrylate and acrylic acid, in an 85/15 ratio, is prepared in isododecane by the method of Example 1 of EP-A-749,746, heptane being replaced by isododecane. A dispersion of particles of poly(methyl acrylate/acrylic acid), which are stabilized at the surface in isododecane by a polystyrene/copoly(ethylene-propylene) sequential diblock copolymer sold under the name of Kraton G1701 (Shell), is thus obtained which has a dry matter content of 22.6% by weight and a mean particle size of up to 175 nm (polydispersity: 0.05) and a Tg of 20° C. This copolymer is able to form a film.

Example 2

(Polymer Dispersion)

The dispersion prepared here is distinguished from that of Example 1 by the use of a diblock dimethicone copolyol as stabilizing agent sold under the name DC3225C by Dow Corning.

Example 3

(Polymer Dispersion)

A dispersion of poly(methyl methacrylate) crosslinked with ethylene glycol dimethacrylate is prepared in isododecane by the method of Example 2 of EP0 749 746, Isopar L being replaced by isododecane. A dispersion of particles of poly(methyl methacrylate), which are stabilized on their surfaces in isododecane by a polystyrene/copolytethylene-propylene) sequential diblock copolymer sold under the name of Kraton G1701 (Shell) is thus obtained which has a dry matter content of 19.7% by weight and a mean particle size of 135 nm (polydispersity: 0.05) and a Tg of 100° C. This copolymer is not able to form a film at room temperature.

Example 4

(O/W Foundation)

The following composition is prepared:

| | |
|---|---|
| dispersion of Example | 116.90 g |
| apricot kernel oil | 2.54 g |
| preservatives | 0.50 g |
| solid sodium hydroxide | 0.03 g |
| xanthan gum | 0.17 g |
| carbomer | 0.08 g |
| glycerol/carbomer/propylene glycol (*) | 4.22 g |
| glycerol | 5.91 g |
| stearic acid | 0.25 g |
| stearyl alcohol | 0.42 g |
| sucrose stearate (**) | 1.10 g |
| polyethylene glycol stearate (PEG 8 stearate) | 1.10 g |
| pigments (***) | 10.00 g |
| water | q.s. for 100 g |

(*) Lubragel MS from Guardian
(**) Tegosoft PSE 141G from Goldschmidt
(***) Same mixture as in Example 5

This foundation is prepared by incorporating the fatty substances and emulsifiers in the polymer dispersion at a temperature of 75° C., homogenizing the fatty phase, incorporating the fatty phase in the aqueous phase with stirring, still at 75° C.; maintaining stirring until the composition has completely cooled.

This foundation is more fluid than that of Example 5 and fresher, while having comparable transfer-free properties.

Example 5
(W/O Foundation)

| The following composition is prepared: | |
|---|---|
| dispersion of Example 1 | 20.60 g |
| cyclomethicone | 4.00 g |
| cyclopentasiloxane | 5.00 g |
| dimethicone copolyol in cyclopentasiloxane (****) | 1.80 g |
| nylon powder (filler) | 8.00 g |
| yellow iron oxide coated with PDMS | 1.45 g |
| yellow-brown iron oxide | 0.67 g |
| black iron oxide | 0.25 g |
| titanium oxide | 7.63 g |
| preservatives | 0.40 g |
| fragrance | 0.60 g |
| magnesium sulfate | 0.70 g |
| diglyceryl isostearyl succinate | 0.60 g |
| water | q.s. for 100 g |

(****) Abil Em 97 from Goldschmidt

A foundation is obtained which can be applied to the body, in particular, to the neck and the face. The make-up is natural, matt and resistant to water and exhibits very good transfer-free properties.

This foundation is prepared by predispersing the pigments in the cyclomethicone, homogenizing the fatty phase (surfactant+oil) at 40–50° C., cooling the material, adding the dispersion of Example 1, adding the pigments, and then adding the entire aqueous phase to the preceding fatty phase, first with slow stirring and then with very powerful stirring for 10 min.

Comparison Example
(W/O Foundation)

| The following composition is prepared: | |
|---|---|
| cyclomethicone | 3.65 g |
| cyclopentasiloxane | 21.40 g |
| isododecane | 4.55 g |
| dimethicone copolyol in cyclopentasiloxane (*) | 6.00 g |
| nylon powder (filler) | 8.00 g |
| VA/vinyl butylbenzoate/crotonate copolymer in aqueous dispersion | 20.00 g |
| yellow iron oxide | 1.45 g |
| yellow-brown iron oxide | 0.67 g |
| black iron oxide | 0.25 g |
| titanium oxide | 7.63 g |
| preservatives | 0.40 g |
| fragrance | 0.60 g |
| magnesium sulfate | 0.60 g |
| isostearyldiglyceryl succinate | 2.00 g |
| diisopropyl adipate | 1.00 g |
| water | q.s. for 100 g |

In this Comparison Example, the copolymer and the diisopropyl adipate are added at the end, after emulsification.

A sensory test was conducted with the foundation of Example 5 and of the Comparison Example on several people. The transfer-free test was conducted in the following manner:

(i) A foundation is applied to the face and to the neck per half-face and half-neck;

(ii) After having applied a moisturizing care cream, "Hydrative" from Lancôme; the applied composition is dried in the open air for 10 minutes;

(iii) A cloth collared around the neck for 30 minutes was positioned. The transfer-free properties are graded from 0–7; the higher the figure, the more the foundation has transferred.

The foundation of the invention received the mean grade of 2, against the mean grade 3.5 for the foundation with aqueous polymer dispersion. In addition, for each person in the test, the formula of the invention is always better in terms of being transfer-free.

Furthermore, the people in a given test judged the product of the invention to be easy to spread, soft and with high slip, conferring a homogeneous and adherent make-up with light coverage. The complexion is uniform. The texture of the product is judged as fluid but more consistent on application than that of the product comprising the aqueous polymer dispersion.

Removal of the make-up is conducted with a conventional make-up remover (Galateis from Lancome) without leaving traces of make-up.

Example 6
(W/O Lipstick)

| The following composition is prepared: | |
|---|---|
| dispersion of Example 1 | 32.74 g |
| yellow-brown iron oxide | 4.00 g |
| preservatives | 0.25 g |
| magnesium sulfate | 0.82 g |
| copolymer of vinylpyrrolidone/1-eicosene | 0.44 g |
| vdimethicone copolyol with α, ω ethylene oxide group in PDMS (****) | 2.12 g |
| phenyl(trimethylsiloxy)trisiloxane (20 cSt at 20° C., MW 372) | 0.76 g |
| isostearic acid mono- and diglycerides esterified with succinic acid | 0.71 g |
| cyclododecanol | 0.33 g |
| water | q.s. for 100 g |

Comparison Example
(Lipstick)

| The following composition is prepared: | |
|---|---|
| aqueous dispersion of styrene-acrylate polymer (45%) | 50.00 g |
| yellow-brown iron oxide | 4.00 g |
| preservatives | 0.25 g |
| acrylic gelling agent | 5.00 g |
| polyethylene/polytetrafluoroethylene wax (50/50) | 4.50 g |
| ethyl alcohol | 5.00 g |
| additives | 3.00 g |
| water | q.s. for 100 g |

A sensory test was conducted with the lip product of Example 6 and of the Comparative Example of lipstick on several people. The transfer-free test was conducted under the following conditions:

(i) Application of the lipstick per half-lip;

(ii) Drying in the open air for 2 minutes;

(iii) Evaluation of the transfer by a kiss test on filter paper;

(iv) Removal of make-up with a conventional make-up remover (Galateis from Lancôme).

The lipstick of the invention emerged with transfer-free properties equivalent to those of the lipstick comprising the aqueous polymer dispersion but with improved properties of comfort (less tautness, a feeling of freshness on application) and easier removal of make-up. Furthermore, the product of the invention is easy to apply as a make-up.

Example 7

(W/O Eyeliner)

The following composition is prepared:

| | |
|---|---|
| dispersion of Example 1 | 32.74 g |
| black iron oxide | 15.00 g |
| hydrogenated isoparaffin | 0.77 g |
| magnesium sulfate | 0.82 g |
| vinylpyrrolidone/1-eicosene copolymer | 0.44 g |
| dimethicone copolyol with α, ω ethylene oxide group in PDMS (****) | 2.12 g |
| phenyl(trimethylsiloxy)trisiloxane (20 cSt at 20° C., MW 372) | 0.76 g |
| isostearic acid mono- and diglycerides esterified with succinic acid | 0.71 g |
| methacrylic acid/methoxy(polyethylene glycol) methacrylate/methyl methacrylate copolymer dissolved in water/propylene glycol (i) | 0.38 g |
| propylene glycol | 4.81 g |
| octyldodecanol | 0.33 g |
| water | q.s. for 100 g |

(i) Arlatone 3315 from ICI (surfactant)

This eyeliner was tested on a bare eyelid followed by removal with two conventional make-up removers, Bi-facil and Effacil from Lancôme. The texture is judged to be fluid, possessing slip and adherent, not being runny and rendering the line very distinct and clean, at the edge and at the tip of the line. The line can even be gone over again after drying. The film is homogeneous. The make-up is soft and is easily removed. The comfort is judged to be good.

The disclosure of French priority Application Number 9811694 filed Sep. 18, 1998 is hereby incorporated by reference into the present specification.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A composition for topical application, comprising:
a liquid fatty phase and an aqueous phase, one of the phases being dispersed in the other phase, and said liquid fatty phase comprising surface-stabilized polymer particles in an amount sufficient to confer transfer-free properties to the composition.

2. The composition according to claim 1, wherein the polymer is provided in the form of dispersed particles which are stabilized on their surfaces by at least one stabilizing agent.

3. The composition according to claim 1, wherein the polymer is selected from the group consisting of radical polymers, polycondensates, polymers of natural origin and their mixtures.

4. The composition according to claim 3, wherein the polymer is selected from the group consisting of polyurethanes, polyurethane-acrylics, polyureas, polyurea-polyurethanes, polyester-polyurethanes, polyether-polyurethanes, polyesters, polyesteramides, polyesters with a fatty chain or alkyds, acrylic polymers or copolymers, vinyl polymers or copolymers, acrylic-silicone copolymers, polyacrylamides, silicone polymers, fluorinated polymers and their mixtures.

5. The composition according to claim 1, wherein the polymer is a film forming polymer.

6. The composition according to claim 1, wherein the liquid fatty phase contains at least one carbon-comprising, hydrocarbon-comprising, fluorinated or silicone oil of mineral, animal, plant or synthetic origin or mixtures thereof.

7. The composition according to claim 1, wherein the liquid fatty phase is selected from the group consisting of liquid parafin or liquid petrolatum, mink oil, turtle oil, soybean oil, perhydrosqualene, sweet almond oil, calophyllum oil, palm oil, parlean oil, grape seed oil, sesame oil, maize oil, rapeseed oil, sunflower oil, cottonseed oil, apricot oil, castor oil, avocado oil, jojoba oil, olive oil, cereal germ oil, an ester of lanolic acid, of oleic acid, of lauric acid, of stearic acid; a fatty ester; a higher fatty acid; a higher fatty alcohol; an optionally phenylated silicone oil, silicone oil optionally substituted by aliphatic and aromatic groups, silicone oil optionally substituted by aliphatic or aromatic groups or by hydroxyl, thiol or amine groups, alone or in combination; a polysiloxane modified by fatty acid, fatty alcohol or polyoxyalkylene, fluorinated silicones or a perfluorinated oil; and volatile oil.

8. The composition according to claim 7, wherein said fatty ester is isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, di(2-ethylhexyl)succinate, diisostearyl malate, glyceryl triisostearate or diglyceryl triisostearate, said higher fatty acid is myristic acid, palmitic acid, stearic acid, behenic acid, oleic acid, linoleic acid, linolenic acid or isostearic acid, said higher fatty alcohol is cetanol, stearyl alcohol, oleyl alcohol, linoleyl or linolenyl alcohol, isostearyl alcohol or octyldodecanol, said silicone oil is phenyltrimethicone, and said volatile oil is isododecane, octamethylcyclotetrasiloxane, decamethylcyclopentasiloxane, hexadecamethylcyclohexasiloxane, heptamethylhexyltrisiloxane, heptamethyloctyltrisiloxane or a $C_8$–$C_{16}$ isoparaffin.

9. The composition according to claim 1, wherein the liquid fatty phase is selected from the group consisting of:
non-aqueous liquid compounds having an overall solubility parameter according to the Hansen solubility space of less than 17 $(MPa)^{1/2}$, or
monoalcohols having an overall solubility parameter according to the Hansen solubility space of less than or equal to 20 $(MPa)^{1/2}$,—or their mixtures.

10. The composition according to claim 1, wherein the liquid fatty phase comprises at least one volatile oil.

11. The composition according to claim 1, wherein the liquid fatty phase is from 5–97.5% of the total weight of the composition.

12. The composition according to claim 2, wherein the stabilizing agent is a sequential polymer, grafted polymer, random polymer or mixtures thereof.

13. The composition according to claim 11, wherein the stabilizing agent is a silicone polymer having a hydrocarbon-comprising chain grafted thereto, a hydrocarbon-comprising polymer having a silicone chain grafted thereto, grafted copolymers having an insoluble polyacrylic backbone with soluble grafts of poly(12-hydroxystearic acid), grafted or sequential block copolymers comprising at least one block of polyorganosiloxane and at least one block of a radical polymer, grafted or sequential block copolymers comprising at least one block of polyorganosiloxane and at least one block of a polyether; copolymers of $C_1$–$C_4$ alkyl acrylates or methacrylates and of $C_8$–$C_{30}$ alkyl acrylates or methacrylates; grafted or sequential block copolymers comprising at least one block resulting from diene polymerization and at least one block of a vinyl polymer; grafted or sequential block copolymers comprising at least one block resulting from diene polymerization and at least one block of an acrylic polymer, or grafted or sequential block copolymers comprising at least one block resulting from diene polymerization and at least one block of a polyether.

14. The composition according to claim 12, wherein the stabilizing agent is a grafted or sequential block copolymer comprising at least one block resulting from diene polymerization and at least one block of a vinyl polymer or comprising a polyoxypropylenated or polyoxyethylenated block or mixtures thereof and a block resulting from the polymerization of a siloxane.

15. The composition according to claim 1, further comprising at least one additional fatty phase selected from the group consisting of waxes, gums, pasty fatty substances of plant, animal, mineral, synthetic or silicone origin and their mixtures.

16. The composition according to claim 1, further comprising at least one coloring material.

17. The composition according to claim 16, wherein the coloring material comprises a pulverulent compound selected from the group consisting of fillers, pigments, pearlescent agents and combinations thereof.

18. The composition according to claim 17, wherein the pulverulent compound is present in an amount up to 50% of the total weight of the composition.

19. The composition according to claim 1, wherein the polymer represents up to 60% of the total weight of the composition.

20. The composition according to claim 1, which is provided in the form of an oil-in-water or water-in-oil emulsion, of a multiple emulsion or of an oil-in-water dispersion by virtue of vesicles comprising ionic or nonionic lipids or mixtures of ionic or nonionic lipids.

21. The composition according to claim 1, which is provided in the form of a product for either the care of and the make-up or the care of or the make-up of the skin, the lips, keratinous fibers or combinations thereof.

22. The composition according to claim 1, which is provided in the form of a foundation, of a face powder, of an eyeshadow, of a lipstick, of a care or protective balm for the lips, of a mascara, of an eyeliner, of a make-up for the body, of an antisun cream or of a cream for the artificial tanning of the skin.

23. The composition according to claim 1, which further comprises at least one cosmetic or dermatological active principle.

24. A method of manufacturing a cosmetic composition or a dermatological composition, comprising:
formulating a dispersion of a first phase in a second phase, either the first or second phase being a liquid fatty phase containing a sufficient amount of surface stabilized polymer particles, in order to at least decrease the transfer of a composition film deposited on mucous membranes, on the skin, on keratinous fibers or combinations thereof of human beings to a substrate brought into contact with the film.

25. A method for the cosmetic care of or for the make-up of the lips, skin, keratinous fibers or combinations thereof, which comprises:
applying to the lips, skin, fibers or combinations thereof, a cosmetic composition as defined in claim 1.

26. A method for at least limiting the transfer of a first composition for the make-up or for the care of skin, lips, keratinous fibers or combinations thereof onto a substrate other than said skin, lips, keratinous fibers or combinations thereof, comprising:
applying a second composition in the form of a dispersion of a first phase in a second phase, one of said phases being a liquid fatty phase containing a sufficient amount of surface-stabilized polymer particles which enable at least limiting the transfer of said first composition, onto said substrate. the other said phase being an aqueous phase. onto said skin, lips. keratinous fibers or combinations thereof having said first composition thereon.

* * * * *